(12) United States Patent
Dastjerdi et al.

(10) Patent No.: US 11,871,981 B2
(45) Date of Patent: Jan. 16, 2024

(54) METHOD OF POWER DISTRIBUTION

(71) Applicant: Medtronic, Inc., Minneapolis, MN (US)

(72) Inventors: Ahmad Khayer Dastjerdi, Toronto (CA); Michael Same, Toronto (CA); Neil Godara, Milton (CA)

(73) Assignee: Medtronic, Inc., Minneapolis, MN (US)

( * ) Notice: Subject to any disclaimer, the term of this patent is extended or adjusted under 35 U.S.C. 154(b) by 674 days.

(21) Appl. No.: 16/722,561

(22) Filed: Dec. 20, 2019

(65) Prior Publication Data

US 2020/0197070 A1 Jun. 25, 2020

Related U.S. Application Data

(60) Provisional application No. 62/782,663, filed on Dec. 20, 2018.

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/14* (2013.01); *A61B 2017/00199* (2013.01); *A61B 2018/00023* (2013.01); *A61B 2018/00434* (2013.01); *A61B 2018/00577* (2013.01); *A61B 2018/00708* (2013.01);
(Continued)

(58) Field of Classification Search
CPC ................ A61B 18/1206; A61B 18/14; A61B 2017/00199; A61B 2018/00708; A61B 2018/124; A61B 2018/00779
See application file for complete search history.

(56) References Cited

U.S. PATENT DOCUMENTS 6,346,104 B2 * 2/2002 Daly .................. A61B 18/1477
606/41
9,717,552 B2 8/2017 Cosman et al.
(Continued)

FOREIGN PATENT DOCUMENTS

EP 2260779 A2 12/2010
WO WO 2018/116247 A1 6/2018

OTHER PUBLICATIONS

International Searching Authority, International Search Report and Written Opinion for PCT/US2019/067818 dated Apr. 3, 2020, 17 pages.

*Primary Examiner* — Sean W Collins
(74) *Attorney, Agent, or Firm* — Patterson Thuente, P.A.

(57) ABSTRACT

A method and apparatus are disclosed for using a generator having insufficient power to supply power to a number of electrosurgical probes during ramping up of the probes to reach set point temperatures. The method includes reducing energy delivery to at least one probe by temporarily disabling energy delivery thereto. Some embodiments comprise a method of delivering energy to at least two electrosurgical probes connected to at least two of the channels of a generator wherein the generator has a maximum output, the method comprising: (a) activating channels which are to be activated; (b) checking for disabling conditions; and (c) if there are disabling conditions, disabling the channel which takes the least power amongst all active channels.

19 Claims, 3 Drawing Sheets

(51) Int. Cl.
*A61B 17/00* (2006.01)
*A61B 18/00* (2006.01)

(52) U.S. Cl.
CPC ............ *A61B 2018/00779* (2013.01); *A61B 2018/00791* (2013.01); *A61B 2018/00875* (2013.01); *A61B 2018/00886* (2013.01); *A61B 2018/124* (2013.01); *A61B 2018/126* (2013.01); *A61B 2018/1253* (2013.01)

(56) References Cited

U.S. PATENT DOCUMENTS

| | | | |
|---|---|---|---|
| 2005/0010206 A1* | 1/2005 | Nasab | A61B 18/1492 606/41 |
| 2008/0097558 A1* | 4/2008 | Eggers | A61B 18/1477 607/101 |
| 2010/0023002 A1* | 1/2010 | DiCarlo | A61B 18/14 606/41 |
| 2010/0324548 A1* | 12/2010 | Godara | A61B 18/1492 606/34 |
| 2014/0276789 A1 | 9/2014 | Dandler et al. | |
| 2017/0319259 A1 | 11/2017 | Dunning | |
| 2020/0008867 A1* | 1/2020 | McGregor | A61B 18/1206 |

* cited by examiner

METHOD OF POWER DISTRIBUTION

CROSS-REFERENCE TO RELATED APPLICATION

This application claims the benefit of U.S. Application Ser. No. 62/782,663, filed Dec. 20, 2018, the disclosure of which is hereby incorporated by reference.

FIELD

The disclosure relates to electrosurgical methods. In particular, it relates to power distribution to a plurality of electrosurgical probes.

SUMMARY

The problem of a generator having insufficient power to supply power to a number of electrosurgical probes (e.g., 2, 3 or 4) during ramping up of the probes to reach a set point temperature is solved by reducing energy delivery to at least one probe by temporarily stopping (or disabling) energy delivery thereto.

In a first broad aspect, embodiments of the present invention comprise a method of delivering energy to at least two electrosurgical probes connected to at least two of the channels of a generator wherein the generator has a maximum output, the method comprising:
(a) activating channels;
(b) checking for disabling conditions; and
(c) if there are disabling conditions, disabling at least one channel, e.g., the channel which takes the least power, the channel which takes the most power or another channel from amongst all active channels.

Typically, step (a) includes activating all channels at the same time. In typical embodiments, step (b) includes checking if at least two electrosurgical probes are active and at least one channel is in a ramping phase. Typical embodiments further comprise step (b) including checking if a total requested power for all channels is greater than the maximum output of the generator, and that step (b) includes checking if any channel has been disabled, or enabled, or stopped by a user, within a first system reaction time (e.g., within the last X seconds).

In some embodiments of the first broad aspect, step (b) includes checking: if the temperature error for all active channels which are in ramping is more than a programmed temperature error of Y degrees for Z seconds; if the temperature error in all active channels is more than a programmed temperature error of Y degrees for Z seconds; or if a total requested power for all channels is greater than an output power limit of the generator for a period of time of Z' seconds.

Typical embodiments of the method of the first broad aspect further comprise a step (d) of checking for enabling conditions and, if there are enabling conditions, a step (e) of re-enabling the most recently disabled channel.

In typical embodiments, step (d) further comprises checking if there is at least one channel disabled by the algorithm or checking if any channel has been disabled, or enabled, or stopped by a user, within a second system reaction time (e.g., the last XX sec).

In typical embodiments of the first broad aspect, checking for enabling conditions (step (d)) includes checking if total power used by all active channels is less than (Ptotal−safety factor YY×Plast for system waiting time enabling ZZ seconds) wherein Ptotal is the total requested power across all channels at time T, and wherein Plast is the last output power of the channel disabled at time T, and wherein time T is the time at which the most recently disabled and not currently enabled channel was shut off.

In some embodiments of the method, step (d) includes checking if total power used by all active channels is less than a selected power level threshold having a safety factor (e.g., YY' Watt).

In a second broad aspect, embodiments of the present invention comprise an electrosurgical system for delivering energy to tissue comprising:
a generator having a maximum output and at least two channels;
at least two probes operable to be connected to the at least two channels such that the two channels are operable to deliver energy; and
a control system, when the at least two probes are connected to the at least two channels, being operable for
(a) activating channels;
(b) checking for disabling conditions; and
(c) if there are disabling conditions, disabling at least one channel, e.g., the channel which uses the least power, or the channel which uses the most power, or some other channel amongst all active channels.

Typically, step (a) includes activating the channels at the same time. In typical embodiments of the second broad aspect, the control system is operable to perform further functions comprising a step (d) of checking for enabling conditions, and if there are enabling conditions, a step (e) of re-enabling the most recently disabled channel.

BRIEF DESCRIPTION OF THE DRAWING

In order that the invention may be readily understood, embodiments of the invention are illustrated by way of examples in the accompanying drawing, in which.

DETAILED DESCRIPTION

Figure 1:
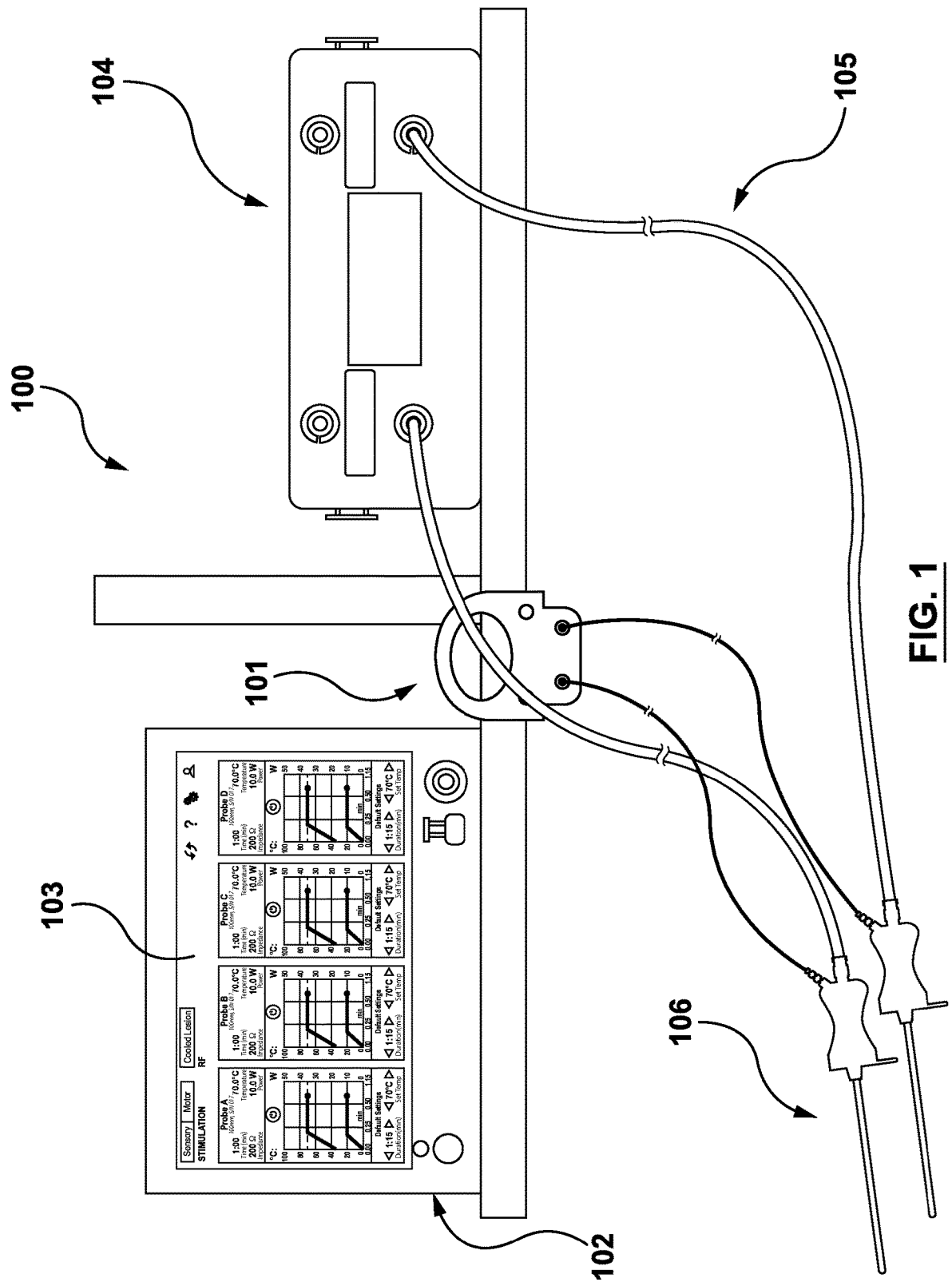
FIG. 1 is an illustration of an embodiment of a system.

The problem of a generator not having sufficient power to supply power to for a number of probes (e.g., 2, 3 or 4) during ramping up of the probes to reach a set point temperature can be solved by reducing energy delivery to at least one probe by temporarily stopping (or disabling) energy delivery thereto. During ramping up (viz., the ramping phase) power is supplied to a probe to increase its temperature to a set temperature (a pre-determined threshold).

Radiofrequency (RF) ablation is a minimally invasive procedure used to treat patients with chronic pain. In this technique, one or more electrodes of one or more electrosurgical probes are placed next to the target nerve. Delivery of radiofrequency current to the target nerve through the electrode generates heat lesion which is neuro-destructive and leads to the interruption of the pain signals to the brain, thus eliminating pain. Variation in the anatomical targets along with the size of the targets necessitates creation of heat lesions with different sizes. Existing systems in the market typically support up to four electrodes simultaneously. In most cases, running procedures with four electrodes simultaneously requires a high power RF generator. However, due to regulatory constrains typical existing generators have a 50 W power limit which is not adequate to handle situations in which several simultaneous large lesions are needed to complete a procedure. Generators having power limits higher than 50 watts (e.g., a 100 watt power limit) can also have similar situations in which the generator power limit is not adequate. The method disclosed herein can also be used with such generators Such underpowered situations have led to development of a method in which systems start channels in a staggered fashion where one electrode begins RF delivery while others are disabled. Once the active channel finishes the ramp up time which requires the highest power, the second electrode becomes active and begins RF delivery. This process progressively continues until all electrodes become active. A staggered start may be able to handle an underpowered situation, but it results in a significant delay in the duration of procedures (e.g., it may double the duration of some procedures). While a staggered start seems to be a practical method to handle underpowered situations, there are some situations in which systems can handle a simultaneous start of 2 or 3 electrodes, and then the other electrodes being enabled once the active electrodes have passed the ramp up time. In such situations, a staggered start will unnecessarily increase a procedure time. Furthermore, the stagger start method fails to handle underpowered situations wherein the total steady state power (power after the completion of ramping) is greater than the total output power of the generator.

The present inventors have conceived of and reduced to practice embodiments of systems and methods for all of a number of probes reaching a set temperature (a pre-determined threshold) when powered by a generator, the systems and methods including an algorithm for a controller of a generator system. In typical embodiments, the set temperature can be different for each channel. The disclosed method may include checking a combination of different conditions to determine the state of the system. There are two states during a procedure in which the system may require adjustment: 1) when the system is power limited and requires disabling a channel (viz., conditions in which the algorithm determines there is in an underpowered situation and disables an active channel), and 2) when the system has enough power available to enable an already disabled channel. In typical embodiments a disabled channel delivers no energy viz., zero energy. In some alternative embodiments a disabled channel delivers energy at a low level. Typically, a channel is disabled by the algorithm and generator, and a channel is stopped by a user. With typical embodiments of the algorithm, a channel which is stopped by a user will not be re-enabled. The algorithm may be used with monopolar energy delivery, bi-polar energy delivery, or a combination of monopolar and bi-polar.

With specific reference now to the drawings in detail, it is stressed that the particulars shown are by way of example and for purposes of illustrative discussion of certain embodiments of the present invention. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1 illustrates an exemplary embodiment of an electrosurgical system 100 implementing the disclosed method. Electrosurgical system 100 includes hub 101 which is a cooled RF hub and allows for the connection of up to four cooled RF probes 106. Alternative embodiments of system 100 do not include hub 101 and the probes are electrically connected to the generator at the RF board. Some alternative embodiments of the system include standard (un-cooled) probes and the appropriate corresponding apparatus.

Generator 102 electrically connects with hub 101 via a cable (or other means) not shown in the figure. GUI 103 (a graphical user interface) is on the generator 102 and allows for user interaction. Some embodiments of the GUI include a user interface specifically configured for cooled RF energy delivery. In some embodiments, the GUI 103 is capable of displaying status (temperature, power, impedance, and remaining procedure time) of four different channels when delivering RF energy on each of the channels, and each of the channels has corresponding graphs on the screen that show the change in power and temperature over time. A cooled RF probe 106 is used to deliver radiofrequency electrical energy for cooled RF ablation. FIG. 1 illustrates each probe 106 having tubing 105 running to it from the pumping unit 104 which allows for cooling when water is passed through a probe.

Figure 3:
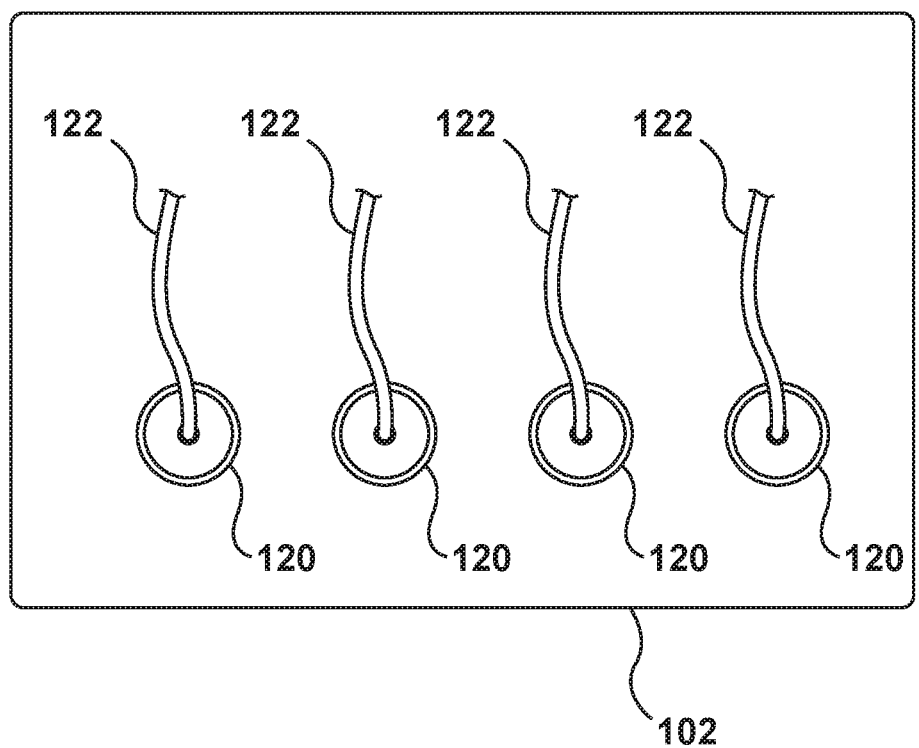
FIG. 3 is a diagrammatic illustration of an embodiment of generator.

FIG. 3 is a diagrammatic illustration of an embodiment of generator 102. The example of FIG. 3 includes 4 of the channel 120, each channel 120 having a single probe wire 122 connected thereto. Alternative embodiments of the generator may for example include two, three or more than four channels. Typically, each channel 120 has only one probe 106 connected to it. Each probe wire 122 is contained inside a cable connected to channel 120. Typical embodiments of generator 102 are operable for monopolar and bi-polar energy delivery. For monopolar energy delivery, a single wire 122 is connected to a probe 106 and a grounding pad is attached to the outside of the patient. Bipolar energy delivery may be achieved using two probes (two probe bipolar) with each probe 106 connected to a unique channel 120 (viz., the two probes are attached to two channels) whereby one probe 106 is an active probe and the second probe is a return probe. Alternatively, bipolar energy can be achieved using a single probe 106 (single probe bipolar) with an active electrode and a return electrode. A probe 106 configured for single probe bipolar can be attached to two channels, with one channel active and the other channel for return, or alternatively the probe 106 could be connected to a single channel for single probe bipolar energy delivery using an adapter (also called a dongle). In the case of two probe bipolar energy delivery (with each probe 106 connected to a unique channel 120) the algorithm accepts the temperature reading of only one of the two probes as an input. The control system software algorithm is typically included in the generator 102.

The algorithm may be operable for cooled RF energy delivery. In alternative embodiments, the algorithm is operable for standard (un-cooled) energy delivery. Some alternative embodiments of generator 101 provide electrical energy outside of the radio frequency range. The disclosed method may be used in systems where a source of energy is required to be distributed across multiple channels but the total available power is not enough to satisfy all channels. The disclosed method may comprise an algorithm which can be implemented in the software of a generator. The algorithm is operable to determine when the system is underpowered and when the system has enough power available to activate a disabled channel.

Embodiments of the electrosurgical system 100 comprise: a generator 102 having a maximum output and at least two channels; at least two probes 106 which are operable to be connected to the at least two channels 120 such that the two channels are operable to deliver energy; and a control system. The control system, when the at least two probes are connected to the at least two channels, is operable for (a) activating the channels which are to be activated; (b) checking for disabling conditions; and (c) if there are disabling conditions, disabling the channel which uses the least power amongst all active channels. Typically, step (a) includes activating the channels at the same time. In alternative embodiments of the system, step (c) includes disabling the channel which uses the most power amongst all active channels or disabling another channel.

Figure 2:
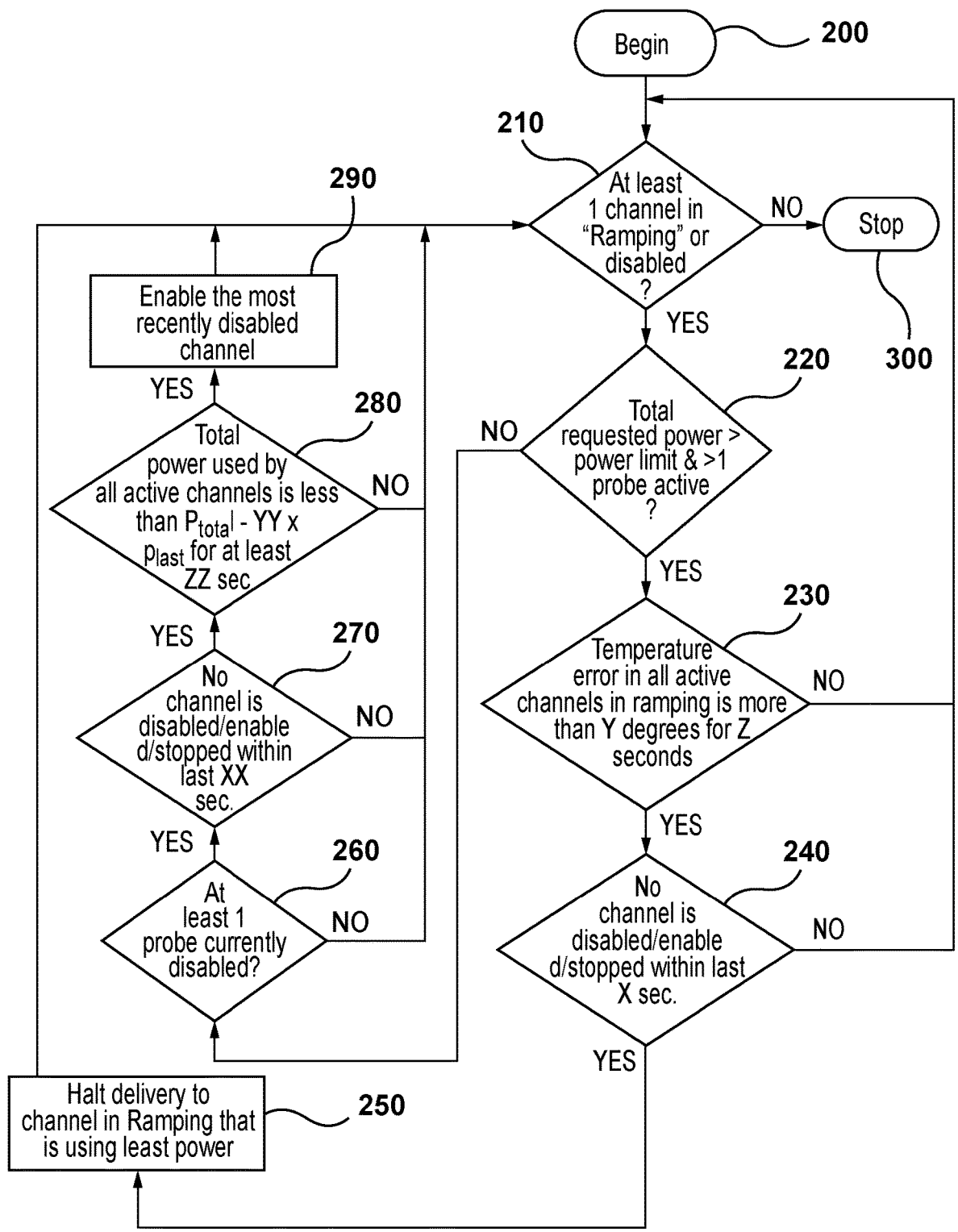
FIG. 2 is a flowchart of an embodiment of a method.

In one embodiment, the disclosed method may employ checking a combination of different conditions to determine the state of the system. Two possible significant states which can occur during a procedure which typically result in a change in the system are: 1) the systems being power limited (viz., underpowered) which results in a channel being disabled, and 2) the system having enough power available to enable a previously disabled channel. FIG. 2 is a flowchart of an embodiment of an algorithm for a method of controlling power distribution. Making reference to FIG. 2, details are provided below about exemplary conditions that may cause the system to disable or re-enable a channel.

The procedure begins at step 200, which comprises the generator activating at least two of the channels of the generator. Typically, step (a) includes activating the channels (which are to be activated) at the same time.

Disabling a Channel

The conditions for disabling a channel are described with respect to steps 210 to 240. If the conditions of steps 210 to 240 are met, the channel is disabled which is in a ramping phase and takes the least power amongst all active channels which are ramping up (step 250). In alternative embodiments of the method, step 250 includes disabling the channel which uses the most power amongst all active channels or disabling another channel.

Step 210 of the algorithm includes checking if at least one channel is in a ramping phase (viz., being supplied with power to reach a set point temperature). The reason for this condition is typical embodiments of the algorithm are intended to address underpowered situations during the ramping phase of a procedure. Step 210 also includes checking if any probes are disabled. If any probes are disabled or at least one channel is in a ramping phase, the algorithm proceeds to step 220.

If neither of the conditions of step 210 is met, the algorithm branches to step 300, which comprises stopping the algorithm.

Step 220 includes determining if power is at its limit by checking if the total power requested for all probes is greater than the power the generator can produce. The requested power for each channel is the power the controller algorithm determines the channel should receive to maintain the control (or target) temperature and minimize the temperature error. The controller defines the requested power for each channel based on the temperature error of the channel and the controller parameters assigned by the generator specific to that channel. Typically, temperature error is the difference between the control temperature (viz., the chosen set point) and the measured temperature wherein the temperature is often measured by a sensor in a probe connected to the channel. In typical embodiments of the system, the user can select a set point temperature and ramp time for each probe, and the system has default values for the probes. Certain factors could impact the controller parameters applied to a specific channel including the probe size, probe type and channel configuration (monopolar or bipolar). In the case of two probe bipolar energy delivery, typically each probe has a temperature sensor and the temperature reading of the sensor which reads a higher temperature is used for control purposes.

Step 220 also includes checking if the system is engaged in active multi-probe lesioning (e.g., checking if more than one probe is active) since the algorithm is designed for use with at least two channels. The algorithm is intended for multi RF cooled probe or multi standard probe lesioning modes. If only one probe is active or connected (single probe mode) then steps 230 and 240 of the algorithm are not needed. If only one probe is active or the generator is able to produce more power, the algorithm branches off to step 260 so that conditions can be checked for possibly re-enabling a probe (the steps 260 to 290 are performed to check if the conditions are met to re-enable a disabled probe).

Step 230 includes checking if the temperature error in all active channels in ramping is more than Y degrees for Z seconds (a pre-set temperature error) wherein "Y degrees" and "Z seconds" are parameters which typically are pre-set in the system. In some alternative embodiments of the system, these parameters can be selected by a user. This condition being met indicates that the active channels are not being supplied with enough power for the channels to achieve the programmed ramp rate due to an underpowered situation.

Step 240 includes checking that no channel has been disabled, or enabled, or stopped by a user, within the last X seconds (a first system reaction time) wherein "X seconds" is a parameter which is typically pre-set in the system. In some alternative embodiments of the system, this parameter can be selected by a user. This check helps provide or ensure sufficient time for the system or to adapt to changes in conditions.

Step 250 comprises disabling a channel. If the conditions of steps 210 to 240 are met, a channel is disabled which is in a ramping phase and takes the least power amongst all active channels (which are ramping up). In alternative embodiments of the method, step 250 comprises disabling the channel which uses the most power amongst all active channels or disabling another channel. After step 250, the algorithm loops back (returns) to step 210.

Enabling a Disabled Channel

The following conditions, described with respect to steps 260 to 290 (FIG. 2), determine when the system is capable of re-enabling the most recently disabled channel without impacting other active channels. The algorithm branches into step 260 from step 220, as explained above.

Step 260 includes checking that at least one channel is currently disabled by the algorithm since typically only currently disabled channels which have been previously disabled by the generator/algorithm are re-enabled. In typical embodiments of the algorithm, the algorithm does not re-enable channels which have been stopped by user intervention.

Step 270 includes checking if any channel has been disabled, or enabled, or stopped by a user, within the second system reaction time of the last XX seconds wherein "XX seconds" is a parameter which typically is pre-set in the system. In some alternative embodiments of the system, this parameter can be selected by a user. If none of the channels have been disabled or enabled or stopped within the specified time, the algorithm proceeds to step 280. The reason for this test is to provide sufficient time for the system to adapt to the changes in conditions.

A purpose of step 280 is to check if the system currently has enough power to activate another channel. Step 280 includes checking for this using the formula:

Total power (currently used by all active channels)< ($P_{total}YY \times P_{last}$ for system waiting time$_{enabling}$ ZZ sec), where:

(a) $P_{total}$ is the total requested power across all channels at time T, (b) YY is a safety factor margin for buffering available power to avoid an underpowered situation wherein YY has value greater than 1. For example, YY=1.3 provides 30 per cent buffering and YY=1.2 provides 20 per cent buffering;

(c) $P_{last}$ is the last output power of the channel disabled at time T;

(d) Time T is the time at which the most recently disabled and not currently enabled channel was shut off; and (e) ZZ is the time period for the system waiting time$_{enabling}$. System waiting time$_{enabling}$ is a period of time the system waits after any status changes before enabling another channel. A purpose of having a system waiting time is to provide for system stability.

In typical embodiments $P_{total}$ is the total requested power across all channels. In some alternative embodiments $P_{total}$ is, the total power used across all channels (which is the same as the total output power). In some other alternative embodiments, $P_{total}$ is the maximum output power.

The algorithm proceeds to step 290 if the tests/checks of steps 260 to 280 are positive. Step 290 comprises enabling a channel which was previously disabled in step 250. In typical embodiments, the channel being enabled is the most recently disabled channel. This step could also be described as re-enabling or re-starting since said channel was previously enabled before being disabled. In some alternative embodiments, the channel being enabled is the first disabled channel. In other alternative embodiments, the channel being enabled may a channel other than the first or last disabled channel e.g., a random channel. After step 290, the algorithm returns to step 210 (described above).

Alternative Embodiments of the Algorithm

In a first alternative embodiment, the algorithm is simplified by changing the test of step 230 (checking if temperature error in all active channels in ramping is more than Y degrees for Z seconds) to the test of "checking if power is at its limit for Z' seconds" which typically functions to check if a total requested power for all channels is greater than an output power limit of the generator for a period of time of Z' seconds. The condition of the generator being at its highest capacity for a period of time likely indicates the generator is not able to provide enough power to supply the requested power.

In a second alternative embodiment, the algorithm is simplified by changing the test of step 280 "Total power (currently used by all active channels) is less than $P_{total}$–YY×$P_{last}$ for system waiting time$_{enabling}$ ZZ seconds" to the test of "Total power used by all active channels is less than power level threshold YY' Watt". There is more than one way to determine power level threshold YY'. YY' can be calculated using the formula YY'=P_max–P_avg_cannula wherein P_max=maximum output power of the system and P_avg_cannula=average of the peak power that all cannula models (or cooled probe models) need to reach their nominal set temperature. YY' can also be calculated using the formula YY'=P_max–P_max_cannula wherein P_max_cannula=the peak power that all cannula models (or cooled probe models) need to reach their nominal set temperature.

In a third alternative embodiment, the algorithm is simplified by omitting step 230 of checking if "temperature error in all active channels in ramping is more than Y degrees for Z seconds".

In a fourth alternative embodiment, step 220 is simplified by removing one of the condition checks. Specifically, the test of "total requested power>power limit" is removed from step 220, leaving the test of checking for multi-probe lesioning by determining if "more than one probe active".

In a fifth alternative embodiment, step 230 is altered by removing "in ramping" from the test, such that the test "the temperature error in all active channels in ramping is more than a pre-set temperature error of Y degrees for Z seconds" is changed to "the temperature error in all active channels is more than a pre-set temperature error of Y degrees for Z seconds". In other words, the test is expanded to include channels which are not ramping.

In a sixth alternative embodiment, step 230 is altered by removing "in ramping" from the test, and an average of temperature error is used, such that the test "the temperature error in all active channels in ramping is more than a pre-set temperature error of Y degrees for Z seconds" is changed to "the average temperature error of all active channels is more than a pre-set temperature error of Y degrees for Z seconds".

The changes of the above first, second, third, fourth, fifth, and sixth alternative embodiments can be implemented individually or in combination as is feasible e.g., the first and third alternatives would not normally both be implemented simultaneously.

FURTHER EXAMPLES

1. A method of delivering energy to at least two electrosurgical probes connected to at least two of the channels of a generator wherein the generator has a maximum output, the method comprising the steps of:
  (a) activating channels which are to be activated;
  (b) checking for disabling conditions; and
  (c) if there are disabling conditions, disabling at least one channel from amongst all active channels.

2. The method of example 1, wherein step (a) includes activating the channels at the same time.

3. The method of example 1 or example 2, wherein step (b) includes checking if at least two electrosurgical probes are active.

4. The method of any one of examples 1 to 3, wherein step (b) includes checking if at least one channel is in a ramping phase.

5. The method of any one of examples 1 to 4, wherein step (b) includes checking if a total requested power for all channels is greater than the maximum output of the generator.

6. The method of any one of examples 1 to 5, wherein step (b) includes checking if any channel has been disabled, or enabled, or stopped by a user, within a first system reaction time.

7. The method of any one of examples 1 to 6, wherein step (b) includes checking if the temperature error in all active channels which are in ramping is more than a pre-set temperature error.

8. The method of any one of examples 1 to 6, wherein step (b) includes checking if the temperature error for all active channels is more than a pre-set temperature error.

9. The method of any one of examples 1 to 8, wherein step (b) includes checking if a total requested power for all channels is greater than an output power limit of the generator for a period of time.

10. The method of any one of examples 1 to 9, wherein step (c) includes disabling a channel which takes the least power from amongst all active channels.

11. The method of any one of examples 1 to 9, wherein step (c) includes disabling a channel which takes the most power from amongst all active channels.

12. The method of any one of examples 1 to 9, wherein step (c) includes disabling a channel other than channels which take the least power or the most power from amongst all active channels.

13. The method of any one of examples 1 to 12, wherein step (c) includes disabling more than one channel from amongst all active channels.

14. The method of any one of examples 1 to 13, wherein step (c) includes temporarily disabling a channel.

15. The method of any one of examples 1 to 14, further comprising a step (d) of checking for enabling conditions.

16. The method of example 15, wherein if there are enabling conditions, further comprising a step (e) of re-enabling the most recently disabled channel.

17. The method of example 15 or example 16, wherein step (d) includes checking if there is at least one disabled channel.

18. The method of any one of examples 15 to 17, wherein step (d) includes checking if any channel has been disabled, or enabled, or stopped by a user, within a second system reaction time.

19. The method of any one of examples 15 to 18, wherein step (d) includes checking if total power used by all active channels is less than ($P_{total}$−safety factor YY×$P_{last}$ for system waiting time$_{enabling}$) wherein time T is the time at which the most recently disabled and not currently enabled channel was shut off, and wherein $P_{total}$ is the total requested power across all channels at time T, and wherein $P_{last}$ is the last output power channel disabled at time T.

20. The method of any one of examples 15 to 19, wherein step (d) includes checking if total power used by all active channels is less than a selected power level having a safety factor.

21. An electrosurgical system for delivering energy to tissue comprising:
 a generator having a maximum output and at least two channels;
 at least two probes operable to be connected to the at least two channels such that the two channels are operable to deliver energy; and
 a control system, when the at least two probes are connected to the at least two channels, being operable for:
  (a) activating channels which are to be activated;
  (b) checking for disabling conditions; and
  (c) if there are disabling conditions, disabling at least one channel from amongst all active channels.

22. The electrosurgical system of example 21, wherein the control system is operable to activate the channels at the same time.

23. The electrosurgical system of example 21 or example 22, wherein the control system is operable to check if at least two electrosurgical probes are active.

24. The electrosurgical system of any one of examples 21 to 23, wherein the control system is operable to check if at least one channel is in a ramping phase.

25. The electrosurgical system of any one of examples 21 to 24, wherein the control system is operable to check if a total requested power for all channels is greater than the maximum output of the generator.

26. The electrosurgical system of any one of examples 21 to 25, wherein the control system is operable to check if any channel has been disabled, or enabled, or stopped by a user, within a first system reaction time.

27. The electrosurgical system of any one of examples 21 to 26, wherein the control system is operable to check if the temperature error in all active channels which are in ramping is more than a pre-set temperature error.

28. The electrosurgical system of any one of examples 21 to 26, wherein the control system is operable to check if the temperature error for all active channels is more than a pre-set temperature error.

29. The electrosurgical system of any one of examples 21 to 28, wherein the control system is operable to check if a total requested power for all channels is greater than an output power limit of the generator for a period of time.

30. The electrosurgical system of any one of examples 21 to 29, wherein the control system is operable to disable a channel which takes the least power from amongst all active channels.

31. The electrosurgical system of any one of examples 21 to 29, wherein the control system is operable to disable a channel which takes the most power from amongst all active channels.

32. The electrosurgical system of any one of examples 21 to 29, wherein the control system is operable to disable a channel other than channels which take the least power or the most power from amongst all active channels.

33. The electrosurgical system of any one of examples 21 to 32, wherein the control system is operable to disable more than one channel from amongst all active channels.

34. The electrosurgical system of any one of examples 21 to 33, wherein the control system is operable to disable a channel temporarily.

35. The electrosurgical system of any one of examples 21 to 34, wherein the control system is further operable to check for enabling conditions.

36. The electrosurgical system of example 35, wherein if there are enabling conditions, the control system is operable to re-enable the most recently disabled channel.

37. The electrosurgical system of example 35 or example 36, wherein the control system is operable to check if there is at least one disabled channel.

38. The electrosurgical system of any one of examples 35 to 37, wherein the control system is operable to check if any channel has been disabled, or enabled, or stopped by a user, within a second system reaction time.

39. The electrosurgical system of any one of examples 35 to 38, wherein the control system is operable to check if total power used by all active channels is less than ($P_{total}$−safety factor YY×$P_{last}$ for system waiting time$_{enabling}$) wherein time T is the time at which the most recently disabled and not currently enabled channel was shut off, and wherein $P_{total}$ is the total requested power across all channels at time T, and wherein $P_{last}$ is the last output power of the channel disabled at time T.

40. The electrosurgical system of any one of examples 35 to 39, wherein the control system is operable to check if total power used by all active channels is less than a selected power level having a safety factor.

In a further broad aspect, some embodiments of the disclosed method deliver energy to at least two electrosurgical probes connected to at least two of the channels of a generator wherein the generator has a maximum output, the method comprising: (a) activating channels; (b) checking for disabling conditions; and (c) if there are disabling conditions, disabling the channel which takes the least power amongst all active channels. Typically, step (a) includes activating the channels at the same time. In alternative embodiments of the method, step (c) includes disabling the channel which uses the most power amongst all active channels or disabling another channel.

In another broad aspect, some embodiments of the disclosed electrosurgical system deliver energy to tissue using components comprising: a generator having a maximum output and at least two channels; at least two probes operable to be connected to the at least two channels such that the two channels are operable to deliver energy; and a control system, the control system, when the at least two probes are connected to the at least two channels, being operable for (a) activating the channels which are to be activated; (b) checking for disabling conditions; and (c) if there are disabling conditions, disabling the channel which uses the least power amongst all active channels. Typically, step (a) includes activating the channels at the same time. In alternative embodiments of the system, step (c) includes disabling the channel which uses the most power amongst all active channels or disabling another channel.

While the description herein focuses mainly on the application of the system in neurotomy procedures, the disclosed method and apparatus are relevant to and may be used for other procedures including tumor ablation procedures.

The embodiments described above are intended to be exemplary only. The scope of the invention is therefore intended to be limited solely by the scope of the appended claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An electrosurgical system for delivering energy to tissue comprising:
    a generator having a maximum output and at least two channels;
    at least two electrosurgical probes operable to be connected to the at least two channels such that the at least two channels are configured to deliver energy; and
    a control system, when the at least two electrosurgical probes are connected to the at least two channels, being configured to:
        (a) activate at least one channel of the at least two channels which are to be activated;
        (b) check for disabling conditions, where disabling conditions include to check if at least one channel of the at least two channels to be activated is in a ramping phase and to check if at least one channel of the at least two channels has been disabled; and
        (c) in response to disabling conditions, disable at least one channel, of the at least two channels, from amongst all active channels based on whether at least one channel to be activated is in a ramping phase or at least one channel is disabled.

2. The electrosurgical system of claim 1, wherein the control system is operable to activate all of the at least two channels at the same time.

3. The electrosurgical system of claim 1, wherein the control system is configured to check if at least two of the connected electrosurgical probes are active.

4. The electrosurgical system of claim 1, wherein the control system is configured to check if a total requested power for all of the at least two channels is greater than the maximum output of the generator.

5. The electrosurgical system of claim 1, wherein the control system is configured to check if at least one channel, of the at least two channels, has been disabled, or enabled, or stopped by a user, within a first reaction time of the control system.

6. The electrosurgical system of claim 1, wherein the control system is configured to check if a temperature error in all active channels which are in a ramping phase is more than a pre-set temperature error.

7. The electrosurgical system of claim 1, wherein the control system is configured to check if a temperature error for all active channels is more than a pre-set temperature error.

8. The electrosurgical system of claim 1, wherein the control system is configured to check if a total requested power for all of the at least two channels is greater than the maximum output of the generator for a period of time.

9. The electrosurgical system of claim 1, wherein the control system is configured to disable a channel, of the at least two channels, which takes a least amount of power output from the generator from amongst all active channels.

10. The electrosurgical system of claim 1, wherein the control system is configured to disable a channel, of the at least two channels, which takes a largest amount of power output from the generator from amongst all active channels.

11. The electrosurgical system of claim 1, wherein the control system is configured to disable a channel, of the at least two channels, other than channels which take a least amount of power or a largest amount of power from amongst all active channels.

12. The electrosurgical system of claim 1, wherein the control system is configured to disable more than one channel, of the at least two channels, from amongst all active channels.

13. The electrosurgical system of claim 1, wherein the control system is configured to disable a channel, of the at least two channels, temporarily.

14. The electrosurgical system of claim 1, wherein the control system is further configured to check for enabling conditions.

15. The electrosurgical system of claim 14, wherein if there are enabling conditions, the control system is configured to re-enable a most recently disabled channel.

16. The electrosurgical system of claim 1, wherein the control system is configured to check if at least one_channel, of the at least two channels, has been disabled, or enabled, or stopped by a user, within a second reaction time of the control system.

17. The electrosurgical system of claim 1, wherein the control system is configured to check if total power used by all active channels is less than a selected power level having a safety factor.

18. An electrosurgical system for delivering energy to tissue comprising:
   a generator having a maximum output and at least two channels;
   at least two electrosurgical probes operable to be connected to the at least two channels such that the at least two channels are configured to deliver energy; and
   a control system, when the at least two electrosurgical probes are connected to the at least two channels, being configured to:
   (a) activate at least one channel of the at least two channels which are to be activated;
   (b) check for disabling conditions, where disabling conditions include to check if at least one channel of the at least two channels to be activated is in a ramping phase and to check if at least one channel of the at least two channels has been disabled;
   (c) in response to disabling conditions, disable at least one channel, of the at least two channels, from amongst all active channels based on whether at least one channel to be activated is in a ramping phase or at least one channel is disable; and
   wherein the control system is configured to check if total power used by all active channels is less than ($P_{total} \times$ safety factor YY$\times P_{last}$ for system waiting time $_{enabling}$) wherein time T is a time at which a most recently disabled and not currently enabled channel was shut off, and wherein $P_{total}$ is a total requested power across all channels at time T, and wherein $P_{last}$ is a last output power of the most recent channel disabled and not currently enabled at time T, and wherein system waiting time$_{enabling}$ is a period of time the system waits after any status changes before enabling another channel.

19. A method of delivering energy to at least two electrosurgical probes connected to at least two channels of a generator wherein the generator has a maximum output, the method comprising the steps of:
   (a) activating channels which are to be activated;
   (b) checking for disabling conditions including checking if at least one channel of the at least two channels to be activated is in a ramping phase and checking if at least one channel of the at least two channels is disabled; and
   (c) if there are disabling conditions, disabling at least one channel from amongst all active channels based on whether at least one channel to be activated is in a ramping phase or at least one channel is disabled.

* * * * *